(12) United States Patent
Berberich et al.

(10) Patent No.: US 9,918,405 B2
(45) Date of Patent: Mar. 13, 2018

(54) SAMPLE COOLING DEVICE FOR HISTOLOGICAL SAMPLES

(71) Applicant: Leica Biosystems Nussloch GmbH, Nussloch (DE)

(72) Inventors: Markus Berberich, Heidelberg (DE); Michael Eberhard, Ludwigshafen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 954 days.

(21) Appl. No.: 14/294,896

(22) Filed: Jun. 3, 2014

(65) Prior Publication Data
US 2014/0368060 A1 Dec. 18, 2014

(30) Foreign Application Priority Data
Jun. 17, 2013 (DE) .................. 10 2013 211 323

(51) Int. Cl.
| | |
|---|---|
| *H02P 13/00* | (2006.01) |
| *H02P 13/06* | (2006.01) |
| *H05K 7/20* | (2006.01) |
| *G01N 1/31* | (2006.01) |

(52) U.S. Cl.
CPC .............. *H05K 7/20* (2013.01); *H02P 13/00* (2013.01); *G01N 1/31* (2013.01); *Y10T 307/858* (2015.04)

(58) Field of Classification Search
CPC .............. H02P 13/00–13/06; G05F 1/14–1/30
USPC ............................................. 307/130; 62/467
See application file for complete search history.

(56) References Cited

U.S. PATENT DOCUMENTS

| | | | | |
|---|---|---|---|---|
| 3,978,395 | A * | 8/1976 | Legnaioli ................ | H01F 29/02 323/255 |
| 4,216,385 | A * | 8/1980 | Omura .................. | G05D 23/275 307/151 |
| 4,540,892 | A | 9/1985 | Carvalho | |
| 4,843,301 | A | 6/1989 | Belanger | |
| 2002/0041505 | A1* | 4/2002 | Suzui ........................ | H02J 7/35 363/95 |
| 2008/0180976 | A1* | 7/2008 | Taylor ................... | H02J 3/1878 363/100 |

(Continued)

FOREIGN PATENT DOCUMENTS

| | | |
|---|---|---|
| DE | 4410902 | 10/1994 |
| EP | 0444792 | 9/1991 |

(Continued)

*Primary Examiner* — Rexford Barnie
*Assistant Examiner* — Thai Tran
(74) *Attorney, Agent, or Firm* — Hodgson Russ LLP

(57) ABSTRACT

A sample cooling device for histological samples is connectable to a power network for supplying electrical voltage to the device. The sample cooling device comprises a measuring apparatus for measuring a magnitude of an input line voltage present at the sample cooling device, and a transformer having a primary coil that comprises at least three coil pickoffs, and a secondary coil. The sample cooling device further comprises a switching means that connects two of the coil pickoffs to the power network as a function of the magnitude of the input line voltage, so that a magnitude of an output voltage present at the secondary coil has a predefined or predefinable voltage value irrespective of the magnitude of the input voltage. A corresponding method for supplying electrical power to a sample cooling device for histological samples is also disclosed.

5 Claims, 1 Drawing Sheet

(56) References Cited

U.S. PATENT DOCUMENTS

2009/0224712 A1* 9/2009 Izaki ................. F24F 12/006
  318/400.32
2013/0043805 A1* 2/2013 Lochmann ......... H05B 37/0263
  315/250

FOREIGN PATENT DOCUMENTS

| EP | 1921391 | 5/2008 |
|----|---------|--------|
| GB | 434884 | 4/1935 |
| JP | H03111917 | 5/1991 |
| JP | H04111107 | 4/1992 |
| JP | H09204229 | 8/1997 |

* cited by examiner

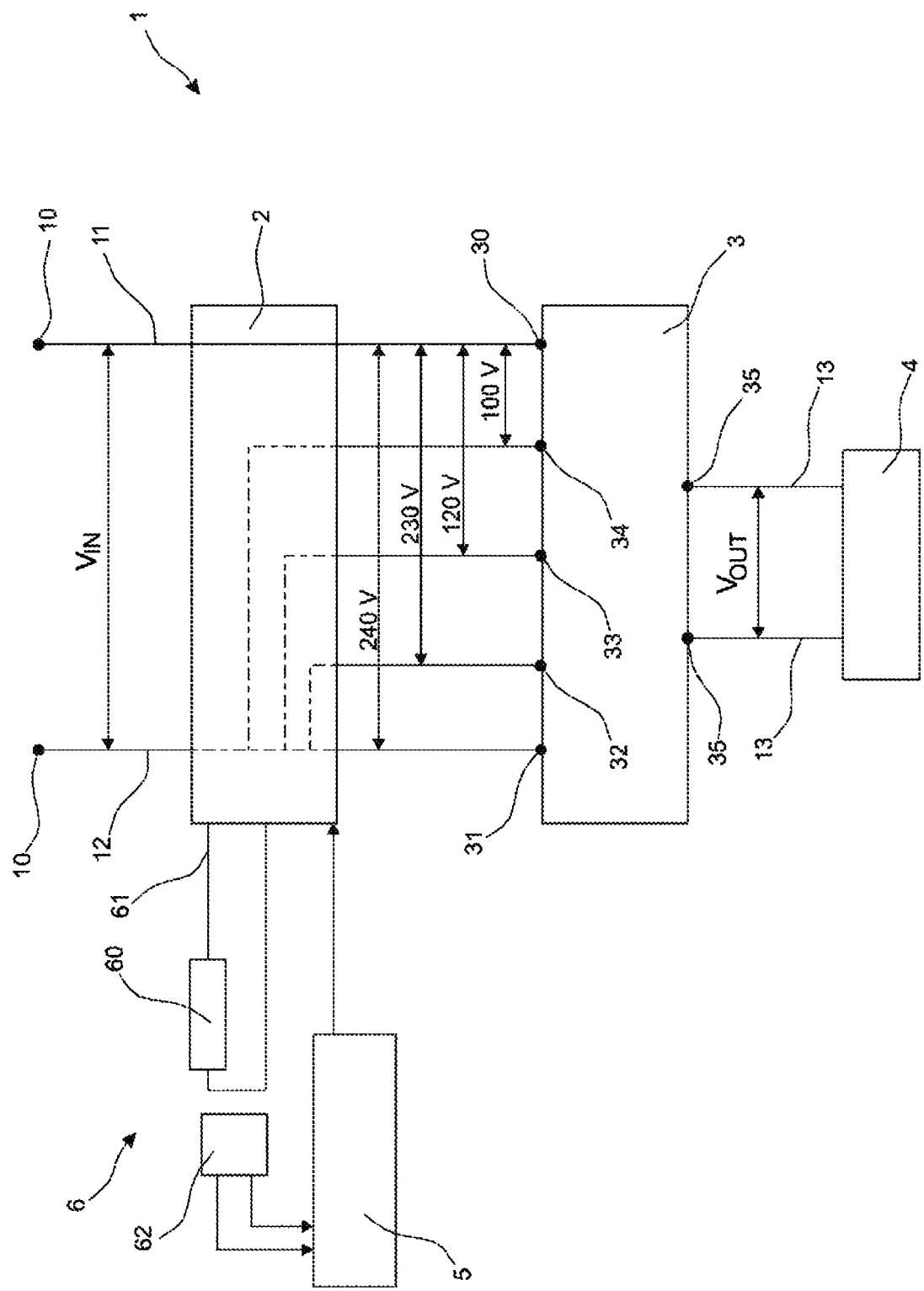

SAMPLE COOLING DEVICE FOR HISTOLOGICAL SAMPLES

CROSS REFERENCE TO RELATED APPLICATIONS

This application claims priority of German patent application number 10 2013 211 323.4 filed Jun. 17, 2013, the entire disclosure of which is incorporated by reference herein.

FIELD OF THE INVENTION

The invention relates to a sample cooling device for histological samples that is connectable to a power network.

The invention further relates to a method for supplying electrical voltage to a sample cooling device for histological samples.

BACKGROUND OF THE INVENTION

A plurality of variously embodied sample cooling devices for histological samples are known from the existing art. The sample cooling devices have in common the fact that they comprise a compressor that, for operation of the sample cooling device, must be connected to a power network. The line voltage furnished by energy suppliers is different in many countries, and can range from 100 V to 240 V. This in turn requires differently configured compressors which are designed so they can be operated with the line voltage existing in the respective country. The result of this is that, because of the different line voltages in the individual countries, manufacturers of sample cooling devices must furnish a plurality of sample cooling device variants that differ from one another in terms of the configuration of the compressor.

A disadvantage of furnishing a plurality of sample cooling device variants is that the production volume of the particular compressor types used for each sample cooling device variant is small, since a different compressor type must be used for each line voltage. Acquisition costs for the individual compressor types are therefore high. Higher administrative and logistical costs also result from the plurality of sample cooling device variants. In addition, damage can occur to the sample cooling devices, in particular to the compressors, if they are supplied with the wrong line voltage.

The object of the invention is therefore to furnish a sample cooling device that is suitable for use in various countries having different line voltages, and thus does not exhibit the disadvantages recited above.

SUMMARY OF THE INVENTION

This object is achieved by the sample cooling device of the kind recited previously which is characterized in that it comprises a measuring apparatus for measuring a magnitude of an input line voltage present at the sample cooling device. The magnitude of the input line voltage can be measured directly or indirectly. The sample cooling device further comprises a transformer having a primary coil that comprises at least three coil pickoffs, and a secondary coil. The sample cooling device furthermore comprises a switching means that connects two of the coil pickoffs to the power network as a function of the magnitude of the input line voltage, so that the magnitude of an output voltage present at the secondary coil has a predefined or predefinable voltage value irrespective of the magnitude of the input line voltage.

A further object of the invention is to furnish a method for supplying electrical power to a sample cooling device for histological samples, which method allows a sample cooling device to be suitable for use in countries having different line voltages, and thus allows the disadvantages recited above not to occur.

This object is achieved by a method of the kind recited previously that comprises the following steps: In a first method step the magnitude of an input line voltage present at the sample cooling device is identified. This is followed by an allocation of the identified magnitude of the input line voltage to two coil pickoffs of a primary coil of a transformer which comprises at least three coil pickoffs, so that a magnitude of an output voltage present at the secondary coil has a predefined or predefinable voltage value irrespective of the magnitude of the input line voltage. Lastly, the allocated coil pickoffs are connected to a power network.

The advantage of the sample cooling device and method according to the present invention is that utilization of the sample cooling device in various countries having different input line voltages is possible. This means that it is no longer necessary to provide sample cooling device variants having differently embodied compressors. It is thereby possible to reduce both sample cooling device costs and administrative and logistical costs. Furthermore, there is no longer any risk that the sample cooling device will become damaged if it is impinged upon by an input line voltage for which the compressor is not designed.

The sample cooling device and method according to the present invention ensure that the compressor is always impinged upon by the predefined or predefinable voltage value irrespective of the input line voltage.

As a result of the allocation of the two coil pickoffs, the number of windings of the primary coil through which the primary current flows can be adjusted as a function of the input line voltage. In particular, thanks to the allocation of the coil pickoffs it is possible to ensure that the magnitude of the output voltage at the secondary coil of the transformer always exhibits the predefined or predefinable voltage value. The output voltage can, for example, always be 100 V.

In a particular embodiment, the switching means can comprise at least one manually introducible plug-in bridge for connecting the coil pickoff to the power network. Introduction of the plug-in bridge can be performed by the user before the sample cooling device is connected to the power network. Visual data, for example color markings, which give the user feedback as to where exactly the plug-in bridge must be introduced for a specific input line voltage magnitude, can be stored on the switching means. The result is to make possible a simple configuration of the sample cooling device, in particular of the switching means.

Alternatively or additionally, the switching means can comprise at least one electromechanical switch and/or at least one electronic switch for connecting the coil pickoff to the power network. Such an embodiment can advantageously be embodied in such a way that the switching means is switched, automatically and thus without intervention by a user, in particular on the basis of a control instruction, in such a way that the coil pickoffs allocated to the magnitude of the input line voltage become connected to the power network. The result is a simple configuration of the switching means. In addition, no previous technical knowledge on the part of the user is required, so that even untrained users can connect the sample cooling device to the power network.

The measuring apparatus can comprise a test load for measuring the magnitude of the input line voltage. The test load can be connected via a test lead to the power network, so that a current flows through the test lead and through the test load. Alternatively or additionally, the measuring apparatus can comprise a Hall sensor and/or a voltage sensor and/or a current sensor. The provision of multiple sensors offers the advantage that a redundant and therefore reliable identification of the magnitude of the input line voltage is possible.

The magnitude of the input line voltage can also be determined indirectly. In particular, the magnitude of the input line voltage can be determined by determining, in particular directly, a magnetic field in the test lead. Alternatively or additionally, the magnitude of the input line voltage can be determined by way of a current measurement, in particular a shunt current measurement. The magnitude of the input line voltage can alternatively be determined directly, by directly measuring the voltage.

The measuring apparatus can be connected in data-communication to a control apparatus. In particular, the value identified by the measuring apparatus, in particular the magnitude of the input line voltage, can be conveyed directly to the control apparatus. The switching means can be controlled, in particular by the control apparatus, on the basis of the conveyed value. The result is that with an embodiment of this kind, a circuit of technically simple configuration is implemented in the sample cooling device, said circuit ensuring that the magnitude of the output voltage of the transformer exhibits a predefined or predefinable voltage value and is independent of the input line voltage. The predefined or predefinable voltage value can depend on the type of compressor used in the sample cooling device.

In a particular embodiment, the output voltage of the secondary coil can be present, in particular directly, at a compressor of the sample cooling device. This means that a rectifier is not provided in the circuit of the sample cooling device, and the compressor is thus impinged upon by an alternating voltage.

BRIEF DESCRIPTION OF THE DRAWING VIEWS

The subject matter of the invention is depicted schematically in the drawings and will be described below with reference to the illustration, in which:

FIG. 1 is a schematic drawing of a circuit of the sample cooling device.

DETAILED DESCRIPTION OF THE INVENTION

A circuit 1, depicted in FIG. 1, of a sample cooling device comprises two connecting terminals 10. Circuit 1 is connected via connecting terminals 10 to a power network (not depicted). When circuit 1 is in the connected state, an input line voltage $V_{IN}$ is present between the two connecting terminals 10. The input line voltage $V_{IN}$ can be in a range between 100 V and 240 V.

Circuit 1 further comprises a switching means 2 and a transformer 3. Switching means 2 is connected via a first lead 11 and a second lead 12, in particular directly, to connecting terminals 10. Transformer 3 comprises a primary coil (not depicted) and a secondary coil (not depicted). The primary coil comprises a plurality of coil pickoffs 30 to 34. In the embodiment depicted in FIG. 1, the primary coil comprises five coil pickoffs 30 to 34. The first and the second leads 11, 12 are each connected to one coil pickoff.

The secondary coil is connected via output leads 13, in particular directly, to a compressor 4 of the sample cooling device. An output voltage $V_{OUT}$ is present between the output leads 13, and is also present at compressor 4. The number of windings (not depicted) of the secondary coil through which current flows is not modifiable. This means that the same coil pickoffs 35 of the secondary coil are always connected to output leads 13.

Switching means 2 comprises at least one electromechanical switch and/or electronic switch whose switch position determines the coil pickoffs 30 to 34 of the first primary coil to which first and second leads 11, 12 are connected. Control is applied to switching means 2 by way of a control apparatus 5 that is connected, in particular directly, to switching means 2. Control apparatus 5 is moreover connected to a measuring apparatus 6.

Measuring apparatus 6 serves to measure the input line voltage $V_{IN}$ and comprises a test load 60 that is connected through a test lead 61 to the first and second leads 11, 12. Measuring apparatus 6 furthermore comprises a Hall sensor 62 that measures the magnetic field in test lead 61. Hall sensor 62 is connected, in particular directly, to control apparatus 5, and conveys the measured values to control apparatus 5.

Based on the values identified by measuring apparatus 6, control apparatus 5 sends a control instruction to switching means 2. The switches of switching means 5 are switched, based on the control instruction, in such a way that first and second leads 11, 12 become connected to those coil pickoffs 30 to 34 of the primary coil such that the predefined or predefinable output voltage $V_{OUT}$ is present at the output of the secondary coil.

Switching means 5 depicted in FIG. 1 is embodied in such a way that first lead 11 is always connected to first coil pickoff 30 irrespective of the input line voltage. For an input line voltage $V_{IN}$ having a magnitude of 240 V, switching means 5 switches second lead 12 in such a way that the latter is connected to a second coil pickoff 31. For an input line voltage having a magnitude of 230 V, second lead 12 is connected to a third lead 32, for an input line voltage having a magnitude of 120 V to a fourth coil pickoff 33, and for an input line voltage having a magnitude of 100 V to a fifth coil pickoff 34.

In addition, the output voltage $V_{OUT}$ is constant irrespective of the input voltage $V_{IN}$. The output voltage $V_{OUT}$ can be, for example, 100 V.

REFERENCE CHARACTERS

1 Circuit
2 Switching means
3 Transformer
4 Compressor
5 Control apparatus
6 Measuring apparatus
10 Connecting terminal
11 First lead
12 Second lead
13 Output lead
30 First coil pickoff on primary coil
31 Second coil pickoff on primary coil
32 Third coil pickoff on primary coil
33 Fourth coil pickoff on primary coil
34 Fifth coil pickoff on primary coil
35 Coil pickoffs on secondary coil 60 Test load
61 Test lead
62 Hall sensor
$V_{IN}$ Input line voltage
$V_{OUT}$ Output voltage

What is claimed is:

1. A sample cooling device for histological samples, the sample cooling device being connectable to a power network, wherein the sample cooling device comprises:
   a) a measuring apparatus (6) for measuring a magnitude of an input line voltage ($V_{IN}$) present at the sample cooling device, wherein the measuring apparatus (6) includes a test load connected through a test lead (61) with a Hall sensor that measures a magnetic field in the test lead, and wherein the measuring apparatus (6) further includes at least one of a voltage sensor and a current sensor for measuring a level of the input line voltage ($V_{IN}$);
   b) a transformer (3) having a primary coil comprising at least three coil pickoffs (30-34), and a secondary coil comprising two coil pickoffs;
   c) a switch (2) for selecting two of the primary coil pickoffs for connection with the input line voltage ($V_{IN}$) as a function of the level of the input line voltage ($V_{IN}$), wherein the switch includes at least one of a manually introducible plug-in bridge, an electromechanical switch, and an electronic switch for connecting the primary coil pickoffs with the input line voltage ($V_{IN}$); and
   d) a compressor operable by a predefined voltage and directly connected with the pickoffs of the secondary coil, the transformer configured to transform voltage applied by the pickoffs of the secondary coil into a defined voltage;
   whereby the sample cooling device is usable in power networks having different input line voltages between 100 V and 240 V.

2. The sample cooling device according to claim 1, wherein the measuring apparatus (6) is connected in data-communication to a control apparatus (5).

3. A method for supplying electrical power to a sample cooling device for histological samples, the method comprising the following steps:
   a) providing a sample cooling device, wherein the sample cooling device includes:
      a measuring apparatus (6) for measuring a magnitude of an input line voltage ($V_{IN}$) present at the sample cooling device, wherein the measuring apparatus (6) includes a test load connected through a test lead (61) with a Hall sensor that measures a magnetic field in the test lead, and wherein the measuring apparatus (6) further includes at least one of a voltage sensor and a current sensor for measuring a level of the input line voltage ($V_{IN}$);
      a transformer (3) having a primary coil comprising at least three coil pickoffs (30-34), and a secondary coil comprising two coil pickoffs;
      a switch (2) for selecting two of the primary coil pickoffs for connection with the input line voltage ($V_{IN}$) as a function of the level of the input line voltage ($V_{IN}$), wherein the switch includes at least one of a manually introducible plug-in bridge, an electromechanical switch, and an electronic switch for connecting the primary coil pickoffs with the input line voltage ($V_{IN}$); and
      a compressor operable by a predefined voltage and directly connected with the pickoffs of the secondary coil, the transformer configured to transform voltage applied by the pickoffs of the secondary coil into a defined voltage;
   b) identifying a magnitude of the input line voltage ($V_{IN}$) present at the sample cooling device using the measuring apparatus (6), which includes ascertaining at least one of a current level and a voltage level;
   c) allocating the identified magnitude of the input line voltage ($V_{IN}$) to two of the at least three coil pickoffs (30-34) of the primary coil as a function of the magnitude of the input line voltage ($V_{IN}$), wherein the coil pickoffs are connected with the input line voltage ($V_{IN}$) via the switch; and
   d) connecting the two coil pickoffs to a power network so that an output voltage arising at the secondary coil is present at the compressor;
      whereby power is able to be supplied to the sample cooling device from power networks having different input line voltages between 100 V and 240 V.

4. The method according to claim 3, wherein the magnitude of the input voltage ($V_{IN}$) is conveyed to a control apparatus (5).

5. The method according to claim 4, wherein the control apparatus determines the two coil pickoffs as a function of the identified magnitude of the input line voltage ($V_{IN}$).

* * * * *